US011712281B2

(12) United States Patent
Szymanski et al.

(10) Patent No.: US 11,712,281 B2
(45) Date of Patent: Aug. 1, 2023

(54) FILTERING SYSTEM, APPARATUS, AND METHOD

(71) Applicant: Buffalo Filter LLC, Lancaster, NY (US)

(72) Inventors: Mark C. Szymanski, Buffalo, NY (US); Michael A. Chimiak, Williamsville, NY (US); Kyrylo Shvetsov, Depew, NY (US); Gregory Pepe, Lancaster, NY (US); Samantha Bonano, WIliamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 234 days.

(21) Appl. No.: 16/978,793

(22) PCT Filed: Oct. 25, 2019

(86) PCT No.: PCT/US2019/058149

§ 371 (c)(1),
(2) Date: Sep. 8, 2020

(87) PCT Pub. No.: WO2020/087007
PCT Pub. Date: Apr. 30, 2020

(65) Prior Publication Data
US 2020/0405367 A1  Dec. 31, 2020

Related U.S. Application Data

(60) Provisional application No. 62/750,878, filed on Oct. 26, 2018.

(51) Int. Cl.
| *A61B 18/00* | (2006.01) |
| *B03C 3/011* | (2006.01) |
| *B03C 3/88* | (2006.01) |
| *B03C 3/49* | (2006.01) |
| *B03C 3/41* | (2006.01) |
| *B03C 3/74* | (2006.01) |

(Continued)

(52) U.S. Cl.
CPC .......... *A61B 18/00* (2013.01); *A61B 18/1402* (2013.01); *B03C 3/011* (2013.01);
(Continued)

(58) Field of Classification Search
CPC combination set(s) only.
See application file for complete search history.

(56) References Cited

U.S. PATENT DOCUMENTS

| 1,478,798 A | 12/1923 | Schmidt |
| 3,768,970 A | 10/1973 | Malmin |

(Continued)

FOREIGN PATENT DOCUMENTS

| JP | 50-065072 U | 6/1975 |
| JP | 51-019082 U | 2/1976 |

(Continued)

OTHER PUBLICATIONS

International Search Report for PCT/US2019/058149 completed Feb. 2, 2020, dated Feb. 19, 2020.

*Primary Examiner* — Christopher P Jones
*Assistant Examiner* — Sonji Turner
(74) *Attorney, Agent, or Firm* — Timothy W. Menasco, Esq.; Harter Secrest & Emery LLP

(57) ABSTRACT

Presented are a method and apparatus for evacuation. An exemplary fluid evacuation system includes a surgical apparatus having a fluid conduit therethrough. The system further includes a vacuum tube fluidly coupled with the fluid conduit, and an electrostatic precipitator fluidly coupled with the fluid conduit. Additionally, the system includes a vacuum source fluidly coupled with the vacuum tube, wherein the vacuum source is operable to create a flow of fluid through the fluid conduit, the vacuum tube and the electrostatic precipitator.

17 Claims, 12 Drawing Sheets

(51) Int. Cl.
*B03C 3/019* (2006.01)
*A61B 18/14* (2006.01)
*A61B 17/32* (2006.01)
*A61B 18/20* (2006.01)

(52) U.S. Cl.
CPC ............... *B03C 3/019* (2013.01); *B03C 3/41* (2013.01); *B03C 3/49* (2013.01); *B03C 3/746* (2013.01); *B03C 3/88* (2013.01); *A61B 18/203* (2013.01); *A61B 2017/32007* (2017.08); *A61B 2018/0091* (2013.01); *A61B 2018/00589* (2013.01); *A61B 2018/00601* (2013.01); *A61B 2218/008* (2013.01); *B03C 2201/04* (2013.01); *B03C 2201/26* (2013.01)

(56) References Cited

U.S. PATENT DOCUMENTS

| | | | | |
|---|---|---|---|---|
| 5,226,939 A * | 7/1993 | Nicolas | ............... | A61B 18/00 55/467 |
| 5,578,000 A * | 11/1996 | Greff | ............... | A61B 18/00 604/22 |
| 9,078,562 B2 * | 7/2015 | Poll | ............... | A61M 13/006 |
| 10,405,917 B2 * | 9/2019 | Shvetsov | ............... | A61B 18/14 |
| 2005/0178265 A1 | 8/2005 | Altman et al. | | |
| 2007/0249990 A1 * | 10/2007 | Cosmescu | ............... | A61M 13/003 604/23 |
| 2009/0062791 A1 * | 3/2009 | Lee | ............... | A61B 18/1402 606/45 |
| 2014/0078798 A1 | 3/2014 | Turchi | | |
| 2017/0007295 A1 * | 1/2017 | Geisz | ............... | A61B 17/3421 |
| 2017/0303964 A1 * | 10/2017 | Kellner | ............... | A61M 13/006 |

FOREIGN PATENT DOCUMENTS

| | | |
|---|---|---|
| JP | 53-010178 U1 | 1/1978 |
| JP | 06142551 A | 5/1994 |
| JP | 2007-100635 A | 4/2007 |
| JP | 2013-087821 A | 5/2013 |
| JP | 2016-214553 A | 12/2016 |
| JP | 2018-528011 A | 9/2018 |
| WO | 94/28814 A1 | 12/1994 |

* cited by examiner

FILTERING SYSTEM, APPARATUS, AND METHOD

BACKGROUND OF THE INVENTION

Field of the Invention

The present disclosure relates generally to evacuation and more specifically to increased smoke evacuation capabilities during medical procedures.

Description of Related Art

Toxic or otherwise harmful surgical smoke and aerosol, or plume, may be produced during surgery. For example, when surgical energy is delivered to a cell, heat may be created causing vaporization of intracellular fluid. Vaporizing intracellular fluid increases the pressure inside the effected cell, eventually causing the cell membrane to rupture. A plume of smoke containing water vapor is released into the atmosphere of the operating room or doctor's office. At the same time, the heat created by the surgical energy may char the protein and other organic matter within the cell and may cause thermal necrosis in adjacent cells. The charring of cells may also release harmful contaminants, such as carbonized cell fragments and gaseous hydrocarbons.

BRIEF SUMMARY OF THE INVENTION

In view of the foregoing, it is an object of the present disclosure to provide a method and apparatus for evacuation.

The present disclosure provides for a fluid evacuation apparatus. In a first exemplary embodiment, a fluid evacuation system includes a surgical apparatus having a fluid conduit therethrough. The apparatus further includes a vacuum tube fluidly coupled with the fluid conduit, and an electrostatic precipitator fluidly coupled with the fluid conduit, the electrostatic precipitator including at least one collection surface operable to attract ionized particulate. Additionally, the system includes a vacuum source fluidly coupled with the vacuum tube, wherein the vacuum source is operable to create a flow of fluid through the fluid conduit, the vacuum tube and the electrostatic precipitator, wherein the electrostatic precipitator includes a collection cell that is electrically charged to at least partially capture oppositely charged particulates in the flow of fluid.

In a second exemplary embodiment, a method includes providing a surgical apparatus having a fluid conduit therethrough, providing a vacuum tube fluidly coupled with the fluid conduit, and providing a vacuum source fluidly coupled with the vacuum tube, wherein the vacuum source is operable to create a flow of fluid. The method further includes providing an electrostatic precipitator disposed in the flow of fluid, wherein the electrostatic precipitator is operable to filter a plurality of particulates from a plume without creating resistance to the flow of the plume.

In a third exemplary embodiment, a fluid evacuation system includes a surgical apparatus having a fluid conduit therethrough and a vacuum tube fluidly coupled with the surgical apparatus. A vacuum source is fluidly coupled with the vacuum tube, wherein the vacuum source is operable to create a flow of fluid. The system further includes a valve operable to interrupt the flow of fluid through the surgical apparatus without affecting a pressure created by the vacuum source.

In a fourth exemplary embodiment, an electrostatic precipitator includes a housing having an inlet port and an outlet port in fluid communication. An electrode is located within the housing and electrically coupled with a power source, the electrode operable to ionize a plurality of particulates in a plume. The electrostatic precipitator further includes a collection surface located downstream of the electrode and electrically coupled with the power source, the power source operable to provide an electric charge to the collection surface. Additionally, a collection tray is located under the collection surface and a cleaning element is located within the housing operable to at least partially remove precipitate from the collection surface to the collection tray.

The following will describe embodiments of the present disclosure, but it should be appreciated that the present disclosure is not limited to the described embodiments and various modifications of the disclosure are possible without departing from the basic principle. The scope of the present disclosure is therefore to be determined solely by the appended claims.

BRIEF DESCRIPTION OF THE SEVERAL VIEWS OF THE DRAWINGS

The accompanying drawings are incorporated herein as part of the specification. The drawings described herein illustrate embodiments of the presently disclosed subject matter and are illustrative of selected principles and teachings of the present disclosure. However, the drawings do not illustrate all possible implementations of the presently disclosed subject matter and are not intended to limit the scope of the present disclosure in any way.

DETAILED DESCRIPTION OF THE INVENTION

Figure 1:
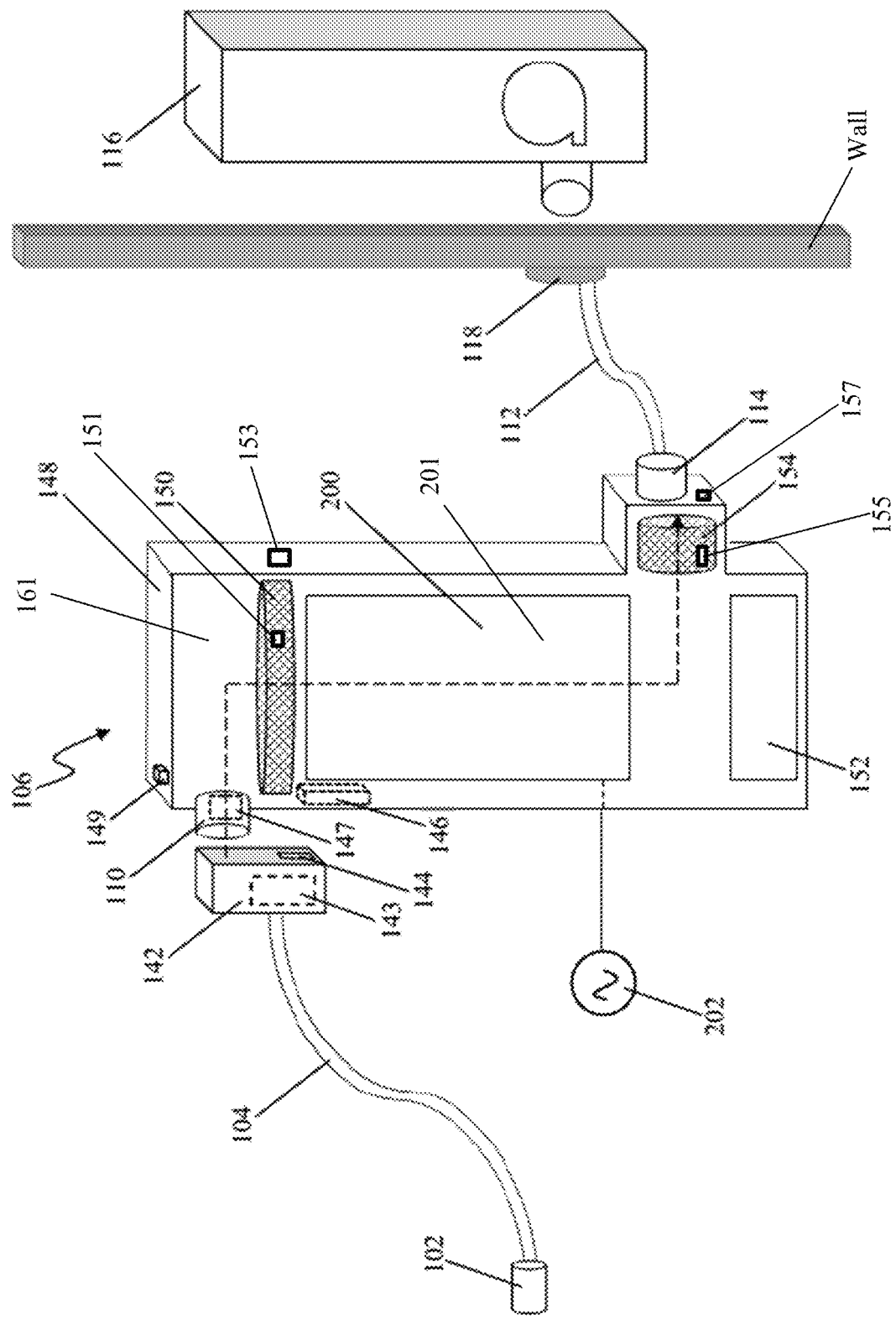
FIG. 1 illustrates a schematic of an exemplary evacuation system according to an embodiment of the present disclosure.

It is to be understood that the invention may assume various alternative orientations and step sequences, except where expressly specified to the contrary. It is also to be understood that the specific assemblies and systems illustrated in the attached drawings and described in the following specification are simply exemplary embodiments of the inventive concepts defined herein. Hence, specific dimensions, directions, or other physical characteristics relating to the embodiments disclosed are not to be considered as limiting, unless expressly stated otherwise. Also, although they may not be, like elements in various embodiments described herein may be commonly referred to with like reference numerals within this section of the application. As used in the following specification, terms of orientation such as "horizontal," "vertical," "left," "right," "up," and "down," as well as adjectival and adverbial derivatives thereof, (e.g., "horizontally," "rightwardly," "upwardly," etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

In view of the above, there remains a need for a fluid evacuation system capable of efficiently and effectively removing at least a portion of the surgical plume created during surgery.

As illustrated in FIG. 1, in an embodiment, an evacuation system 100 (also referred to as a fluid evacuation system) may comprise a surgical apparatus 102 in fluid communication with an electrostatic precipitator assembly 106 via a tube 104. A first end tube 104 may be in sealed connection with a fitting 108 (shown in FIG. 2) disposed at a proximal end of the surgical apparatus 102 and a second end of the tube 104 may be in sealed connection with a fluid inlet 110 of the electrostatic precipitator assembly 106. It should be appreciated that embodiments of tube 104 may be either removeably or fixedly attached forming a sealed connection with fitting 108 and fluid inlet 110. A second tube 112 may comprise a first end in sealed connection with a fluid outlet 114 of the electrostatic precipitator assembly 106 and a second end in sealed connection with a fluid inlet 118 of a vacuum power source 116. Embodiments of second tube 112 include second tube 112 being removeably or fixedly attached forming a sealed connection with fluid inlet 118 and fluid outlet 114. In an embodiment, the vacuum power source 116 may be a central vacuum unit installed in a wall of medical facility or it may be a separate standalone vacuum unit located adjacent to or spaced from the electrostatic precipitator assembly 106. The vacuum power source 116 is operable to create or urge a fluid flow through the surgical apparatus 102, the tube 104, the electrostatic precipitator assembly 106, and the second tube 112.

Figure 2:
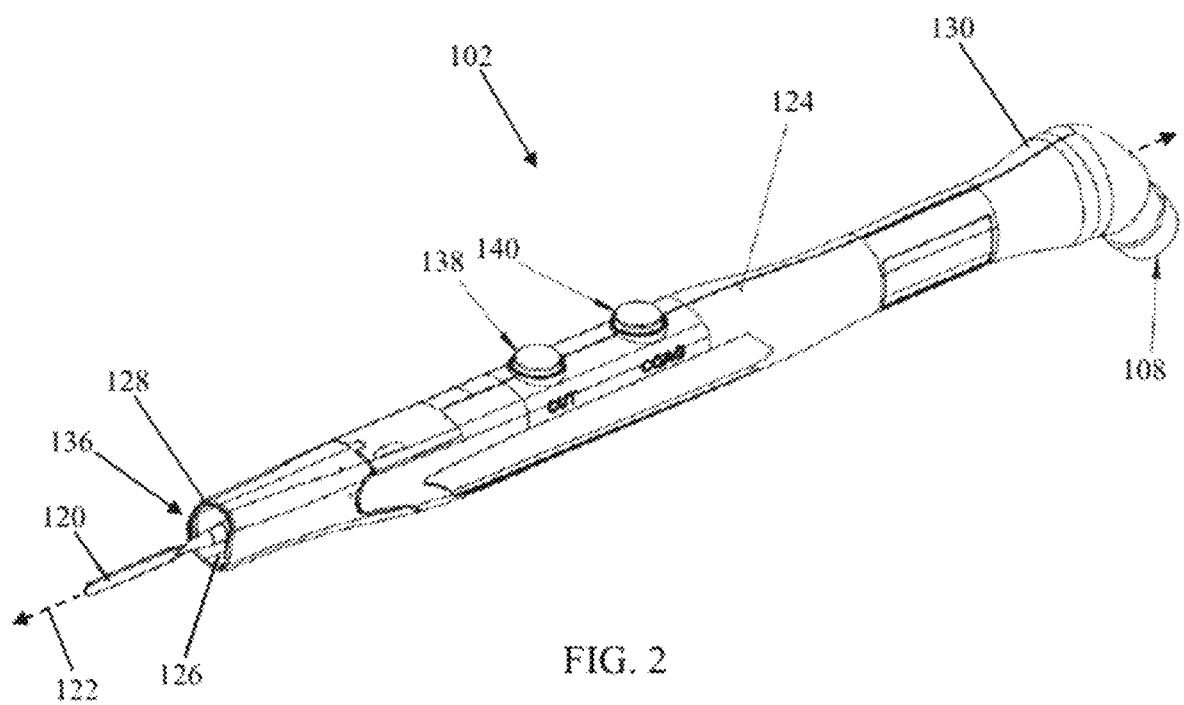
FIG. 2 illustrates an exemplary surgical apparatus according to an embodiment of the present disclosure.
Figure 3:
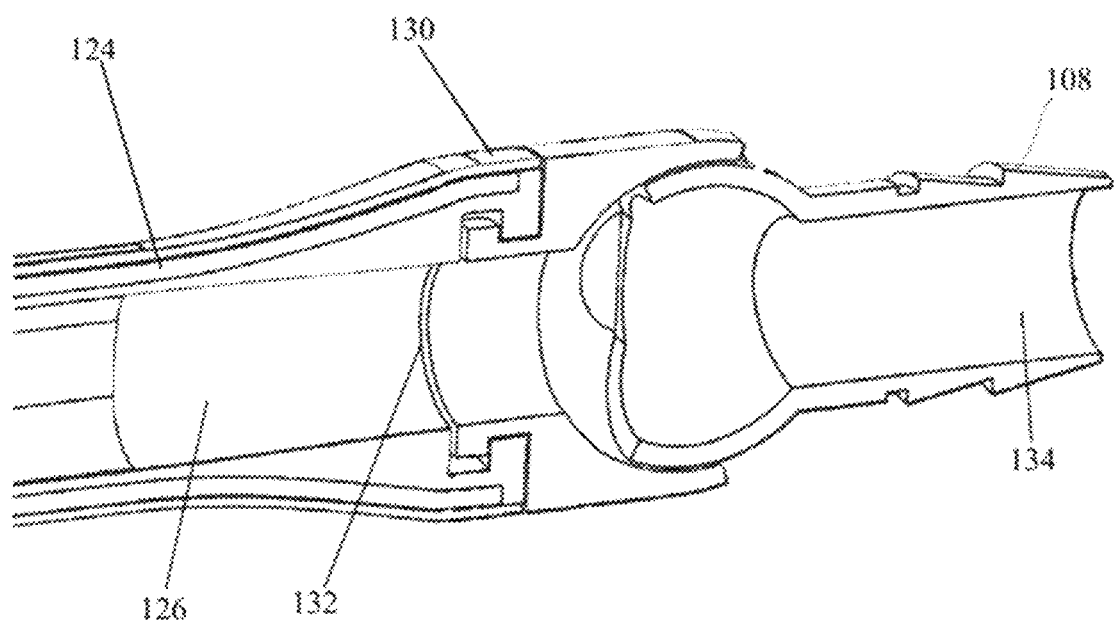
FIG. 3 illustrates a cross sectional view of a portion of an exemplary surgical apparatus.

As illustrated in FIGS. 2 and 3, in an embodiment, the surgical apparatus 102 may include an electrosurgical pencil having a cutting element 120 and a longitudinal axis 122. The surgical apparatus 102 may also comprise a hollow body 124 enclosing a fluid conduit 126 (see FIG. 3). In an embodiment, the fluid conduit 126 may extend coaxially through the longitudinal axis 122 of the electrosurgical pencil hollow body 124 from a distal end 128 to a proximal end 130 thereof. As illustrated in FIG. 2, the cutting element 120 may be disposed at the distal end 128 of the electrosurgical pencil hollow body 124.

Referring now to FIG. 2, in an embodiment, the cutting element 120 may comprise at least one electrode. The at least one electrode 120 may be employed to apply an electrical current to a patient's tissue for cutting and/or coagulation. In other embodiments, the cutting element 120 may comprise, but is not limited to, an ultrasonic scalpel or a laser scalpel.

As illustrated in FIG. 3, a port 132 may be disposed in the proximal end 130 of the electrosurgical pencil hollow body 124 in fluid communication with the fluid conduit 126. In an embodiment, the fitting 108 may comprise a barbed fitting having a fluid conduit 134 disposed therethrough. The fitting 108 is coupled with the electrosurgical pencil proximal end 130 and is in fluid communication with port 132. In other embodiments, the fitting 108 may comprise a connector of other designs. For example, a female connector may be utilized in place of the barbed fitting 108. A female connector may be utilized to keep the inner diameter of the fitting, and hence the fluid conduit 134, as large as possible.

As illustrated in FIG. 2, the electrosurgical pencil distal end 128 may be provided with an inlet 136 in fluid communication with the hollow body fluid conduit 126. During operation of the surgical apparatus 102, surgical smoke generated thereby enters the hollow body inlet 136 and passes through the hollow body fluid conduit 126 to the port 132. From the port 132, surgical smoke is communicated through the fitting 108 to the tube 104. Accordingly, surgical smoke and debris from a procedure may be conveyed through the surgical apparatus 102 to the tube 104. From the tube 104, the surgical smoke and debris are conveyed to the electrostatic precipitator assembly 106. The term surgical smoke may be referred to herein interchangeably with the term plume. It should be appreciated that while embodiments of the present disclosure may be described as being operable to evacuate fluid, smoke and/or plume, embodiments are also operable to evacuate gas, fluid, and/or particulates.

As illustrated in FIG. 2, in an embodiment, the surgical apparatus 102 may be provided with a cut button 138 and a coagulate button 140 that provide different levels of current to the cutting element electrode 120. In one embodiment, the cut button 138 is operable to activate the cutting element electrode 120 at a first power level and the coagulate button 140 is operable to activate the cutting element electrode 120 at a second power level. In an embodiment, the first power level may be higher than the second power level. The cut button 138 and the coagulate button 140 may also be operable to activate the electrostatic precipitator assembly 106. In an embodiment, activating the surgical apparatus 102 also activates the electrostatic precipitator assembly 106 at or about the same time. Deactivating the surgical apparatus 102 may also deactivate the electrostatic precipitator assembly 106 at or about the same time. In an embodiment, the electrostatic precipitator assembly 106 may maintain an activated state for a set period of time after the surgical apparatus 102 is deactivated and before the electrostatic precipitator assembly 106 itself deactivates. It should be appreciated that while FIGS. 2 and 3 illustrate a surgical apparatus 102 as an electrosurgical device, embodiments include surgical apparatus 102 being any type of medical device used in a surgical environment or medical environment in which fluid evacuation is required. For instance, embodiments of surgical apparatus 102 include a trocar, suction devices, and the like.

Figure 11:
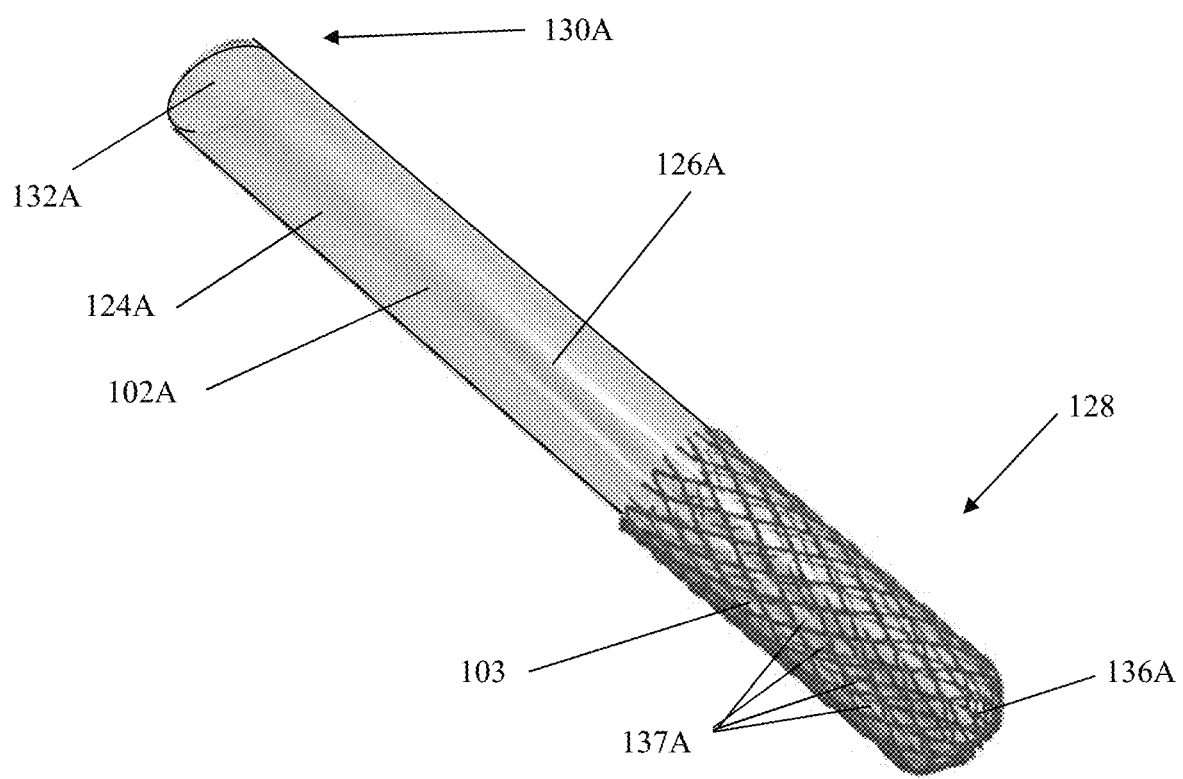
FIG. 11 illustrates another exemplary surgical apparatus according to an embodiment of the present disclosure.

As illustrated in FIG. 11, in another embodiment of the fluid evacuation system 100, the surgical apparatus 102 may comprise a wand 102A. The wand 102A may comprise a hollow generally cylindrical body 124A defining a fluid conduit 126A therethrough. A distal end 128A of the wand 102A may be provided with an inlet 136A and a proximal end 130A of the wand 102A may be provided with an outlet 132A. The wand inlet 136A may be in fluid communication with the wand outlet 132A via the fluid conduit 126A therethrough. The proximal end 130A may be connected with the tube 104 such that the wand outlet 132A is in fluid communication with the tube 104. The wand conduit 126A may include a constant or a variable diameter.

Figure 12:
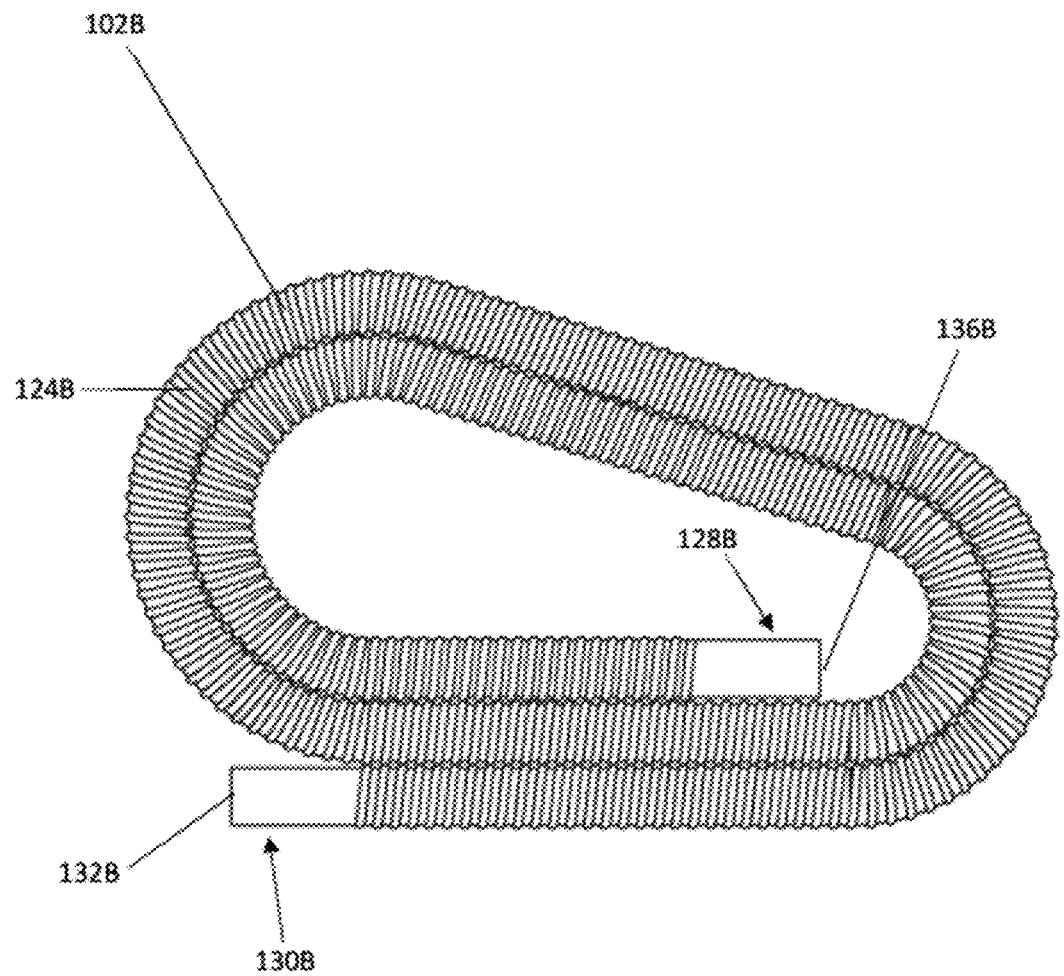
FIG. 12 illustrates another exemplary surgical apparatus according to an embodiment of the present disclosure.

As illustrated in FIG. 12, in another embodiment of the fluid evacuation system 100, the surgical apparatus 102 may be a flexible tube 102B. The flexible tube 102B may comprise a hollow generally cylindrical body 124B defining a fluid conduit therethrough. A distal end 128B of the flexible tube 102B may be provided with an inlet 136B and a proximal end 130B of the flexible tube 102B may be provided with an outlet 132B. The flexible tube inlet 136B may be in fluid communication with the flexible tube outlet 132B via the fluid conduit therethrough. The proximal end 130B may be connected with the tube 104 such that the flexible tube outlet 132B is in fluid communication with the tube 104. In another embodiment, the flexible tube proximal end 130B may be coupled directly with a manifold 142 or the electrostatic precipitator assembly inlet 110. The conduit through the flexible tube 102B may include a generally constant or variable diameter.

In another embodiment, the surgical apparatus 102 may comprise a nozzle defining a variable cross-sectional area. A removable sponge guard 103 (see FIG. 11) may be located about the distal end of the surgical apparatus 102 to prevent inadvertent suctioning of dressings. Embodiments of sponge guard 103 provide a porous flexible netting or covering that is operable to cover the inlet 136A such that larger objects (e.g., sponges, gauze, pads, etc.) cannot enter the fluid conduit 126A. Embodiments of sponge guard 103 are operable to allow smoke, debris, and/or particulates to pass through the plurality of holes 137A of sponge guard 103 so that the smoke, debris, and/or particulates can enter fluid conduit 126A.

As illustrated in FIG. 1, in an embodiment, the manifold 142 may be disposed in the fluid path of the fluid evacuation system 100 between the tube 104 and the electrostatic precipitator assembly 106. The manifold 142 may be mounted to the fluid inlet 110 of the electrostatic precipitator assembly 106 such that the manifold 142 is in fluid communication with the inlet 110. The second end of the tube 104 may be coupled with an inlet of the manifold 142. In another embodiment, the manifold 142 may be mounted internally to the electrostatic precipitator assembly 106, such that the tube 104 is coupled directly with the fluid inlet 110 and fluid outlet 110 is fluidly coupled to manifold 142. The manifold 142 may include a fluid trap 143 for capturing a portion of the surgical smoke. The fluid trap 143 is operable to remove liquid such as, but not limited to, water from the surgical smoke. The manifold 142 may include a window for viewing the level of the liquid captured by the fluid trap 143. In an embodiment, the fluid trap 143 may comprise a cold trap or a condenser.

In an embodiment, the manifold 142 may include a radio-frequency identification tag 144 (RFID) operable to maintain and transmit identifying information of manifold 142 including make, model, and/or status of manifold 142. The status of manifold 142 may include the year manifold 142 was built, a length of time manifold 142 has been in use, and/or whether the fluid trap 143 should be replaced because it is not functioning correctly or is not properly filtering the fluid and particulates that pass-through manifold 142. The electrostatic precipitator assembly 106 may include a RFID reader 146 capable of recognizing the RFID 144 of the manifold 142. The RFID 144 of the manifold 142 may be utilized to ensure component recognition such that fluid evacuation system 100 or electrostatic precipitator 106 only operates when the electrostatic precipitator RFID reader 146 recognizes the manifold 142 having the requisite specifications, make, model, status, and/or whether the fluid trap 143 should be replaced.

The electrostatic precipitator assembly 106 may further comprise a housing 148, a hollow conduit 161 and a valve 147 disposed within the housing 148 at the fluid inlet 110. The fluid inlet 110 and fluid outlet 114 are in fluid communication via the hollow conduit 161. The housing 148 may include the fluid inlet 110 and the fluid outlet 114. In an embodiment, the valve 147 is in fluid communication with fluid inlet 110 and may be operable to interrupt the flow of surgical smoke, fluid, and/or particulates through the electrostatic precipitator assembly 106 at or adjacent to fluid inlet 110 during operation of the vacuum power source 116. As illustrated in FIG. 1, the valve 147 may be located within the electrostatic precipitator fluid inlet 110. In an embodiment, the surgical apparatus 102 will be able to operate valve 117. For instance, the cut button 138 and the coagulate button 140 may be operable to open and close the valve 147, such that when the surgical apparatus 102 is activated the valve 147 is open, and when the surgical apparatus 102 is deactivated the valve 147 is closed. In other embodiments, the open and/or closed state of the valve 147 may be operable by a keypad or a button 149 disposed on or in the housing 148 such that the button 149 is operable by medical staff or a user. It should be appreciated that embodiments of valve 147 include valve 147 being located adjacent to or within outlet 114 such that valve 147 is operable to obstruct or interrupt the flow of surgical smoke, fluid, and/or particulates from entering tube 112.

The electrostatic precipitator assembly 106 may further comprise a particulate filter 150 disposed within the housing 148 in hollow conduit 161. Filter 150 is located downstream and is fluidly connected to fluid inlet 110. The particulate filter 150 may capture any coarse particulates in the surgical smoke or flow of fluid through electrostatic precipitator assembly 106 after entering the electrostatic precipitator assembly 106. The particulate filter 150 is replaceable and removeable from electrostatic precipitator assembly 106 to ensure that particulates accumulated in the particulate filter 150 do not reduce the rate of fluid flow through the electrostatic precipitator assembly 106 below a predetermined threshold. Embodiments include particulate filter 150 having an RFID tag 151 operable to maintain and transmit information such as the make, model, status, and/or filter rates of particulate filter 150. Embodiments further include electrostatic precipitator assembly 106 including an RFID reader 153 operable to communicate with RFID tag 151 to read the information maintained by RFID tag 151. RFID tag 151 and RFID reader 153 may be utilized to ensure component recognition such that electrostatic precipitator 106 continues to operate and filter within predetermined specifications.

With reference to FIG. 1, an electrostatic collection cell 200 may be disposed within the electrostatic precipitator assembly housing 148 in hollow conduit 161 downstream of the particulate filter 150. The collection cell 200 comprises a collection surface 201. Embodiments of the collection surface 201 include a planar or a plurality of planar surfaces operable to be electrically charged such that the collection surfaces 201 are oppositely from an electrode 212 (shown in FIG. 4). An electrical power source 202 is electrically connected with the collection cell 200 to selectively supply electrical current to the collection cell 200. In an embodiment, the electrical power source 202 may be the alternating current (AC) power supply of a building. In another embodiment, the electrical power source 202 may be, but is not limited to, a rechargeable battery or a replaceable battery. In operation, the collection cell 200 induces an electrostatic charge in at least a portion of the particulate suspended in the flow of fluid, surgical smoke, and/or particulates that pass-through electrostatic precipitator assembly 106. At least a portion of the charged particulate is then captured by the collection cell 200 such that the particulates are removed from the flow of fluid, surgical smoke, and/or particulates. The electrostatic collection cell 200 may comprise a one-stage design wherein the electrostatic charge is induced relative to the particulate collection site, or a two-stage design wherein the electrostatic charge is induced in the particulate upstream of the particulate collection site.

In an embodiment, the electrostatic precipitator assembly 106 may also include a collection tray 152 disposed underneath or adjacent to the collection cell 200 such that collection tray 152 may collect, capture, and maintain particulates and other materials from collection cell 200. The collection tray 152 may accumulate particulate removed from the surgical smoke, fluid, and/or particulates by the collection cell 200 that is not maintained on or within the collection cell 200 by the electrostatic force therein. In other words, collection tray 152 is operable to receive and maintain accumulated particulate that does not stay on or within the collection cell 200 because the forces of gravity acting on the accumulated particulate are greater than the electrostatic forces of the collection cell 200, thus causing accumulated particulate to fall or be removed from collection cell 200. The collection tray 152 may be a removeable component, such that when a predetermined amount of particulate accumulates within the collection tray 152, the collection tray 152 may be replaced. In another embodiment, the collection tray 152 may be removeable such that the collection tray 152 may be cleaned of particulate and reinstalled within the electrostatic precipitator assembly housing 148.

A second particulate filter 154 may be disposed within the housing 148 adjacent to the fluid outlet 114. The second particulate filter 154 may capture any coarse particulates in the surgical smoke not removed by the collection cell 200 before they enter the tube 112. The second particulate filter 154 is replaceable to ensure that particulates accumulated therein do not reduce the rate of fluid flow through the electrostatic precipitator assembly 106 below a predetermined threshold. In one embodiment the second particulate filter 154 is a High Efficiency Particulate Air filter. Embodiments include particulate filter 154 having an RFID tag 155 operable to maintain and transmit information such as the make, model, status, and/or filter rates of particulate filter 154. Embodiments further include electrostatic precipitator assembly 106 including an RFID reader 157 operable to communicate with RFID tag 154 to read the information maintained by RFID tag 155. RFID tag 155 and RFID reader 157 may be utilized to ensure component recognition such that electrostatic precipitator 106 continues to operate and filter within predetermined specifications.

Figure 4:
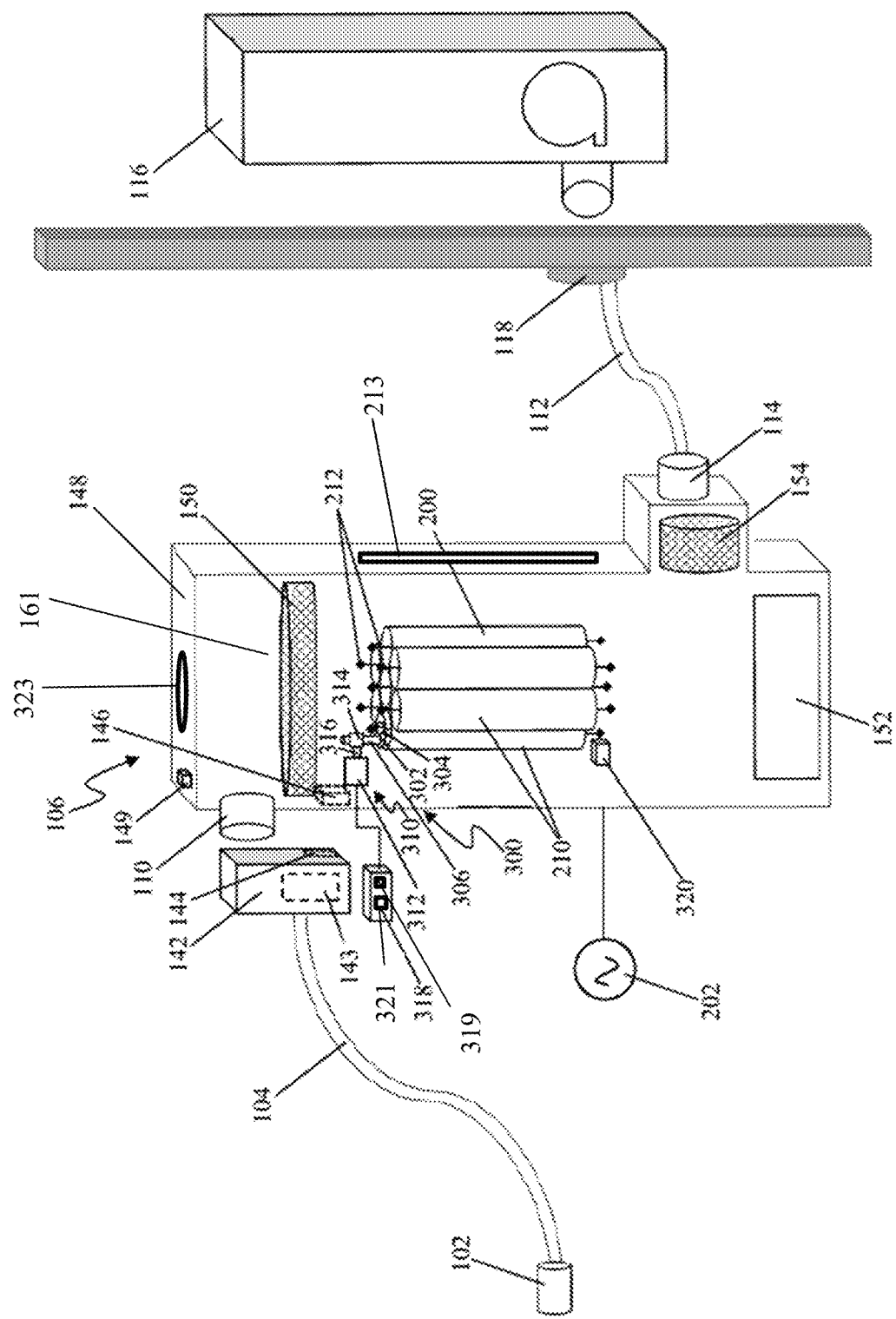
FIG. 4 illustrates a schematic of an exemplary electrostatic precipitator according to an embodiment of the present disclosure.

In an embodiment, as illustrated in FIG. 4, the electrostatic collection cell 200 may comprise a plurality of hollow-cylindrical collection tubes 210. The collection tubes 210 may be disposed in two or more offset rows such that each row may be nested into an adjacent row in a generally honeycomb geometry. In an embodiment, not depicted, the collection tubes 210 may comprise a hollow hexagonal prismatic geometry. The longitudinal axes of the collection tubes 210 may be generally vertically oriented. The electrostatic collection cell 200 may also include a plurality of discharge electrodes 212. The discharge electrodes 212 may be disposed generally coaxially through the collection tubes 210. The discharge electrodes 212 are in electrical communication with the electrical power source 202 for electrically charging particulate within the surgical smoke.

In operation, surgical smoke, fluid, and/or particulates are communicated through the electrostatic precipitator assembly inlet 110 to hollow conduit 161, through the particulate filter 150, then through the collection tubes 210 where the discharge electrodes 212 electrically charge, or ionize, at least a portion of the remaining particulate in the surgical smoke, fluid, and/or particulates. Collection tubes 210 are oppositely charged from the discharge electrodes 212 such that the collection tubes 210 are operable to attract the particulate that is electrically charged by discharge electrodes 212. The ionized particulate is then accumulated on a radially inner collection surface of the collection tubes 210. Ionized particulate not accumulated on the collection tubes 210 may be captured by the collection tray 152. After passing through the collection cell 200, the surgical smoke then passes through the second particulate filter 154 and out the outlet 114.

The collection surface of the collection tubes 210 and the electrodes 212 can be oppositely charged. In an embodiment, the power source 202 may be utilized to induce (i) a negative voltage in the discharge electrodes 212, and (ii) to induce a positive voltage in the collection surface of the collection tubes 210. In another embodiment, the power source 202 may be utilized to induce a negative voltage in the discharge electrodes 212. In this embodiment the collection surface of the collection tubes 210 may be connected to ground. In still another embodiment, the power source 202 may be utilized to induce a positive voltage in the discharge electrodes 212. In this embodiment the collection surface of the collection tubes 210 may be connected to ground or it may have a negative voltage induced therein via the power source 202. In one embodiment, the electric potential difference between the discharge electrodes 212 and the collection surface of the collection tubes 210 is seven kilovolts ("7 kV"). The electric potential difference between the discharge electrodes 212 and the collection surface of the collection tubes 210 may be greater than 7 kV; however, undesirable electric arcing between the discharge electrodes 212 and the collection surface may occur at a high enough electric potential difference.

In an embodiment, the collection tubes 210 may be temporarily removed from the electrostatic precipitator assembly housing 148 to be cleaned prior to reinstallation. Alternatively, or in conjunction with being cleanable, the collection tubes 210 may be disposable and replaceable. In embodiments where the collection surface of the collection tubes 210 are not connected to ground during operation, the opening of an access panel 213 in the housing 148 connects the collection surface to ground. Connecting the collection surface to ground prior to removal ensures the prevention of harm to any person removing the collection tubes 210 from the electrostatic precipitator assembly 106 due to residual voltage in the collection surface.

Figure 13:
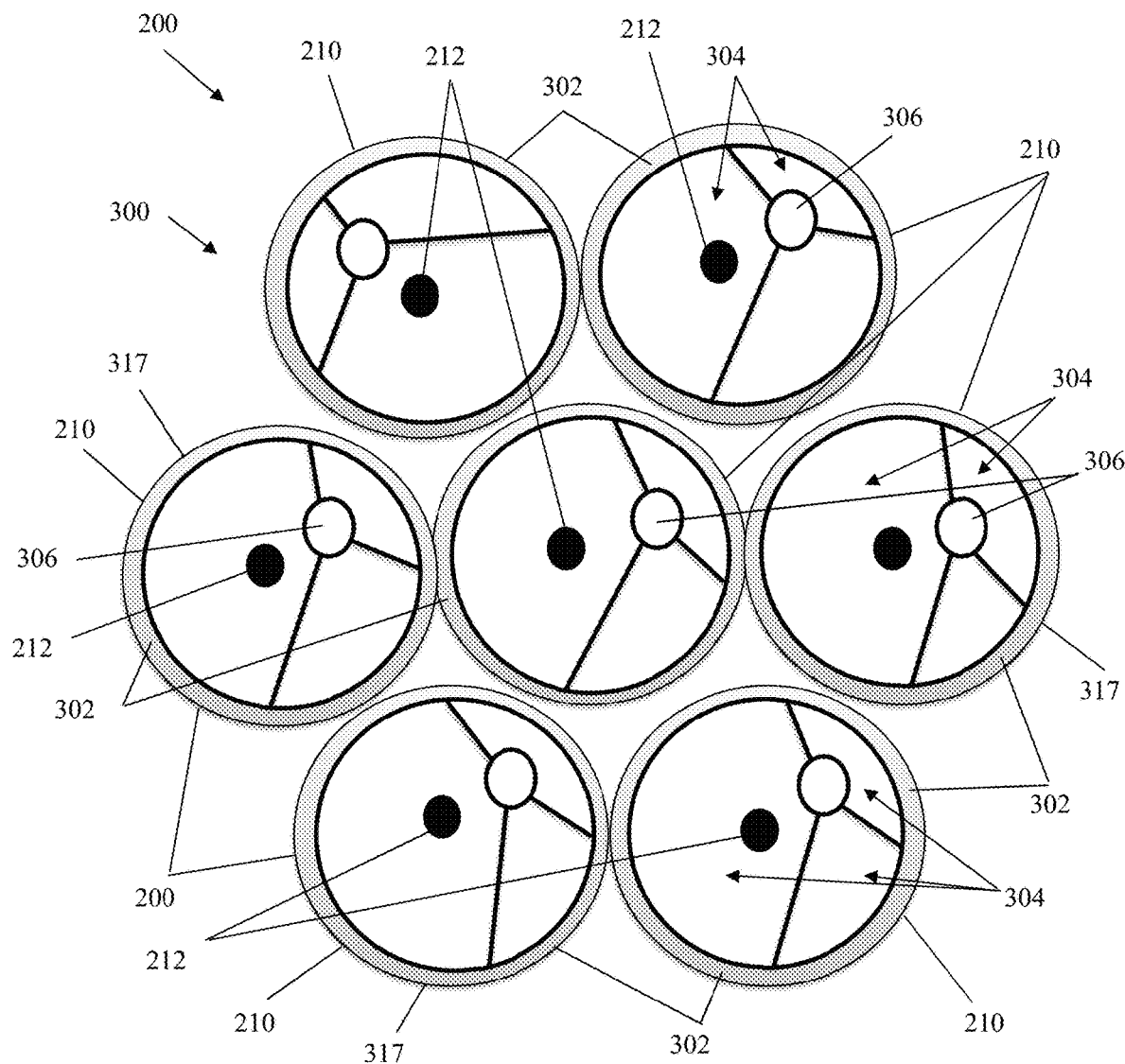
FIG. 13 illustrates a top view of the collection cell 200 shown in FIG. 4

In another embodiment, as illustrated in FIGS. 4 and 13, the electrostatic precipitator assembly 106 may include a cleaning element 300 to at least partially remove the precipitate and accumulated particulate from the collection surface of the collection cell 200. Referring to FIG. 13, shown is a top view of cleaning element 300 depicted in FIG. 4. The cleaning element 300 may comprise a plurality of annular blades 302 located such that each blade 302 may move through one of the collection tubes 210. In other words, each one of the collection of tubes 210 will have a corresponding annular blade 302 for removing accumulated particulate from the radial interior surface of the corresponding one of the collection of tubes 210. The radially outer edge of the blade 302 is disposed such that it will contact the collection surface 317 as the blade 302 moves through the collection tube 210. The collection surface 317 is located on the radial interior surface of collection tubes 210. Blades 302 are operable to move through the longitudinal axis of collection tubes 210 such that accumulated particulate is removed from collection surface 317. In an embodiment, the blade 302 may comprise an elastomeric material. One or more apertures 304 may be disposed through the blade 302 to accommodate the discharge electrode 212 disposed therethrough. Additionally, the blade 302 may be fixedly coupled with a first shaft 306 capable of linear actuation within the housing 148. An actuator assembly 310 may be located within the housing 148 to actuate the blade 302 through the collection tube 210. In an embodiment, the actuator assembly 310 may comprise a power source 312 such as a brushless direct current (BLDC) motor. The power source 312 may be coupled with a pinion gear 314 via a shaft 316. The pinion gear 314 may be in meshed engagement with a plurality of teeth on the shaft 306. In other embodiments, the actuator assembly 310 may comprise other linear actuators.

Actuation of the blade 302 through the collection tube 210 slides the blade 302 along the interior radial collection surface 317 of the collection tube 210 removing particulate to the collection tray 152. Blades 302 may be actuated through the other collection tubes 210 via the power source 312. In other embodiments, the additional blades 302 may be actuated by additional actuator assemblies 310. The actuator assembly 310 may be electrically connected with a controller 318. In an embodiment, the controller 318 may be in communication with at least one sensor 320 capable of detecting a change in the electrical charge of at least one collection surface. When the sensor 320 transmits a signal to the controller 318 indicating that the electrical charge of at least one collection surface has decreased below a predetermined voltage (due to a build-up of accumulated particulates on the collection surface shielding or reducing the electrical charge), the controller 318 operates the actuator assembly 310. In an embodiment, the sensor 320 may comprise a Hall-effect sensor. The sensor 320 may transmit signals to the controller 318 via radio wireless communication or a wired connection.

Figure 5:
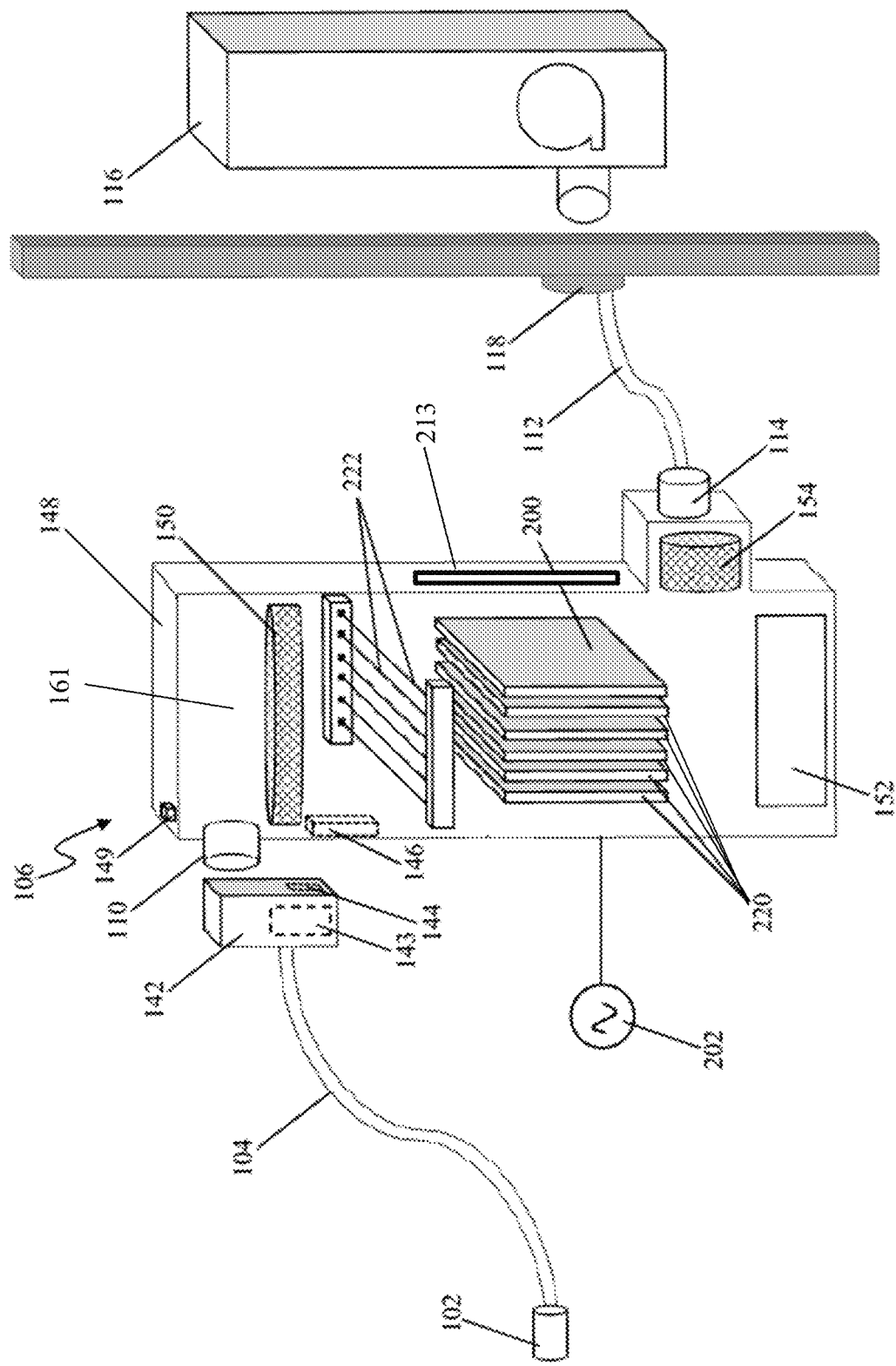
FIG. 5 illustrates another schematic of an exemplary electrostatic precipitator according to an embodiment of the present disclosure.

In another embodiment, as illustrated in FIG. 5, the electrostatic collection cell 200 may comprise a plurality of collection plates 220. The collection plates 220 may be disposed generally parallel to one another in a generally vertical plane. In this embodiment, the electrostatic collection cell 200 may also include a plurality of horizontally disposed discharge electrodes 222 located upstream of the collection plates 220. In operation, surgical smoke, fluid, and/or particulates are communicated through the electrostatic precipitator assembly inlet 110, through the particulate filter 150, then over and around the discharge electrodes 222 where at least a portion of the remaining particulate in the surgical smoke, fluid, and/or particulates are electrically charged or ionized. The surgical smoke, fluid, and/or particulates then pass between the collection plates 220 where the ionized particulate is accumulated on a collection surface thereof. Ionized particulate not accumulated on the collection plates 220 may be captured by the collection tray 152. Embodiments provide that collection tray 152 is located beneath collection plates 220 such that excess ionized particulate can fall through hollow conduit 161 on to collection tray 152 after a predetermined amount of particulate accumulates on the surface of collection plates 220. The predetermined amount of accumulated particulate to cause additional ionized particulate to fall will occur when the amount of ionized particulate on the surface of collection plates 220 is operable to block additional ionized particulate from being attracted to collection plates 220 such that the forces of gravity are greater than the magnetic pull between ionized particulate and the collection plates 220. After passing through the collection cell 200, the surgical smoke then passes through the second particulate filter 154 and out the outlet 114.

The collection surface of the collection plates 220 and the discharge electrodes 212 are oppositely charged. In an embodiment, the power source 202 may be utilized to induce a negative voltage in the discharge electrodes 222 and to induce a positive voltage in the collection surface of the collection plates 220. In another embodiment, the power source 202 may be utilized to induce a negative voltage in the discharge electrodes 222, and the collection surface of the collection plates 220 may be connected to ground. In still another embodiment, the power source 202 may be utilized to induce a positive voltage in the discharge electrodes 222, and the collection surface of the collection plates 220 may be connected to ground or have a negative voltage induced therein via the power source 202. In one embodiment, the electric potential difference between the discharge electrodes 222 and the collection surface of the collection plates 220 is seven kilovolts ("7 kV"). The electric potential difference between the discharge electrodes 222 and the collection surface of the collection plates 220 may be greater than 7 kV; however, undesirable electric arcing between the discharge electrodes 222 and the collection surface may occur at a high enough electric potential difference.

In an embodiment, the collection plates 220 may be temporarily removed from the electrostatic precipitator assembly housing 148 to be cleaned prior to reinstallation. Alternatively, or in conjunction with being cleanable, the collection plates 220 may be disposable and replaceable. In embodiments where the collection surface of the collection plates 220 is not connected to ground during operation, the opening of an access panel 213 in the housing 148 connects the collection surface to ground. Connecting the collection surface to ground prior to removal ensures the prevention of harm to any person removing the collection plates 220 from the electrostatic precipitator assembly 106 due to residual voltage in the collection surface.

Figure 6:
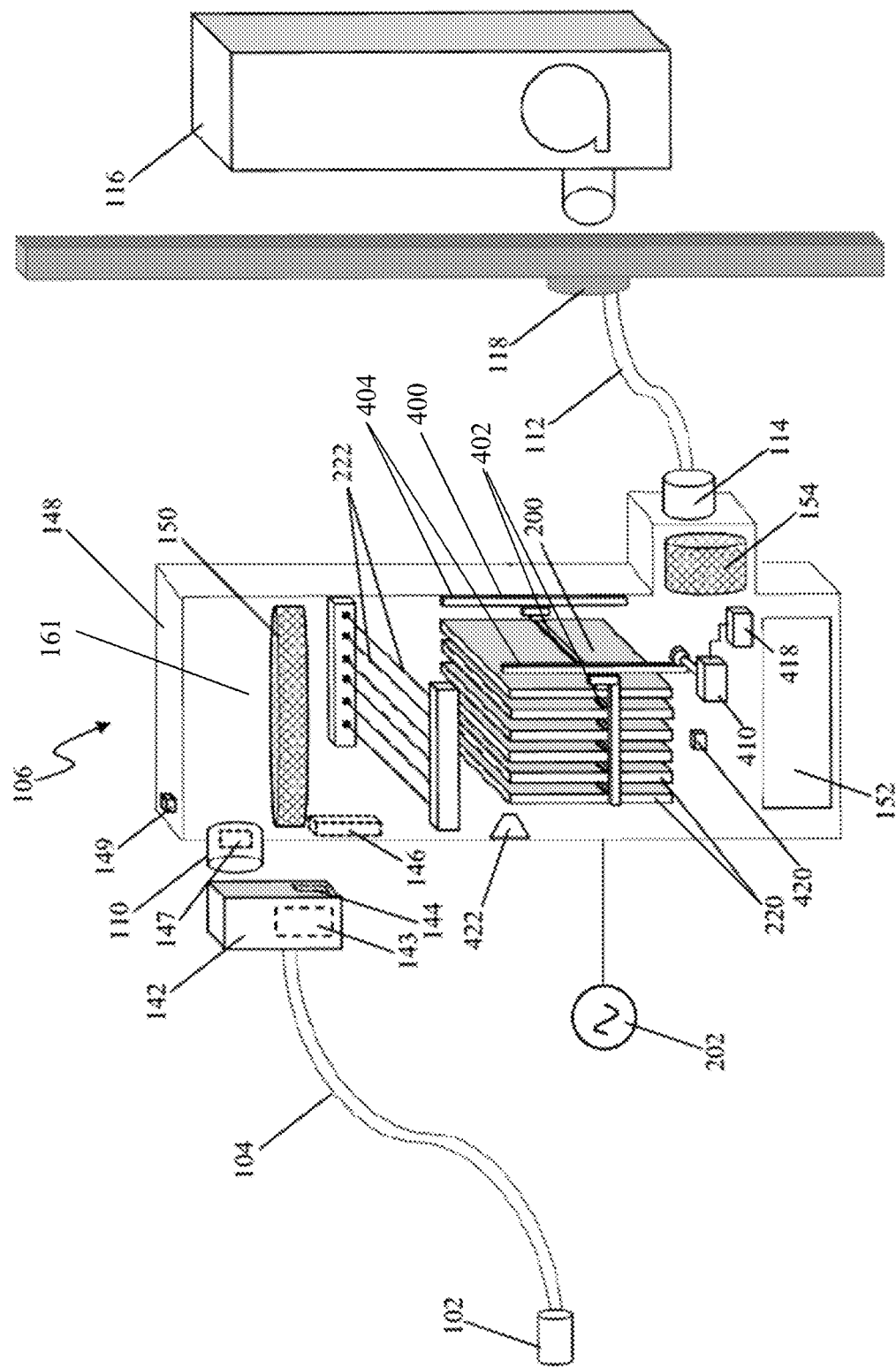
FIG. 6 illustrates another schematic of an exemplary electrostatic precipitator according to an embodiment of the present disclosure.

Referring now to FIG. 6, in another embodiment, the electrostatic precipitator assembly 106 may include a cleaning element 400 to at least partially remove the precipitate and accumulated particulate from the collection surface of the collection cell 200. The cleaning element 400 may include a plurality of blades 402. Each of the blades 402 may be disposed between two of the plates 220 on an exterior planar surface of plates 220. The blades 402 may be made of an elastomeric material. The opposing edges of each blade 402 are in contact with the collection surfaces of the collection plates 220 during actuation of the blades 402. The blades 402 may be coupled with a transversely disposed arm 404 operably coupled with an actuation assembly 410.

The actuator assembly 410 may be electrically connected with a controller 418. In an embodiment, the controller 418 may be in communication with at least one sensor 420 capable of detecting a change in the electrical charge of at least one collection surface. When the sensor 420 transmits a signal to the controller 418 indicating that the electrical charge of at least one collection surface has decreased below a predetermined voltage, the controller 418 operates the actuator assembly 410 such that blades 402 are moved to remove accumulated particulate from the surface of plates 220. In an embodiment, the sensor 420 may comprise a Hall-effect sensor. The sensor 420 may transmit signals to the controller 418 via radio wireless communication or a wired connection.

In an embodiment, the cleaning element 400 may include a nozzle 422 operable to spray fluid onto the collection surface of the collection plates 220 to at least partially remove precipitate therefrom and into the collection tray 152. The nozzle 422 may be utilized independently from the blades 402 or in conjunction therewith. Nozzle 422 may be operably coupled to controller 418 such that controller 418 can activate or deactivate nozzle 422 to selectively spray fluid onto the collection surface of the collection plates 220.

Figure 9:
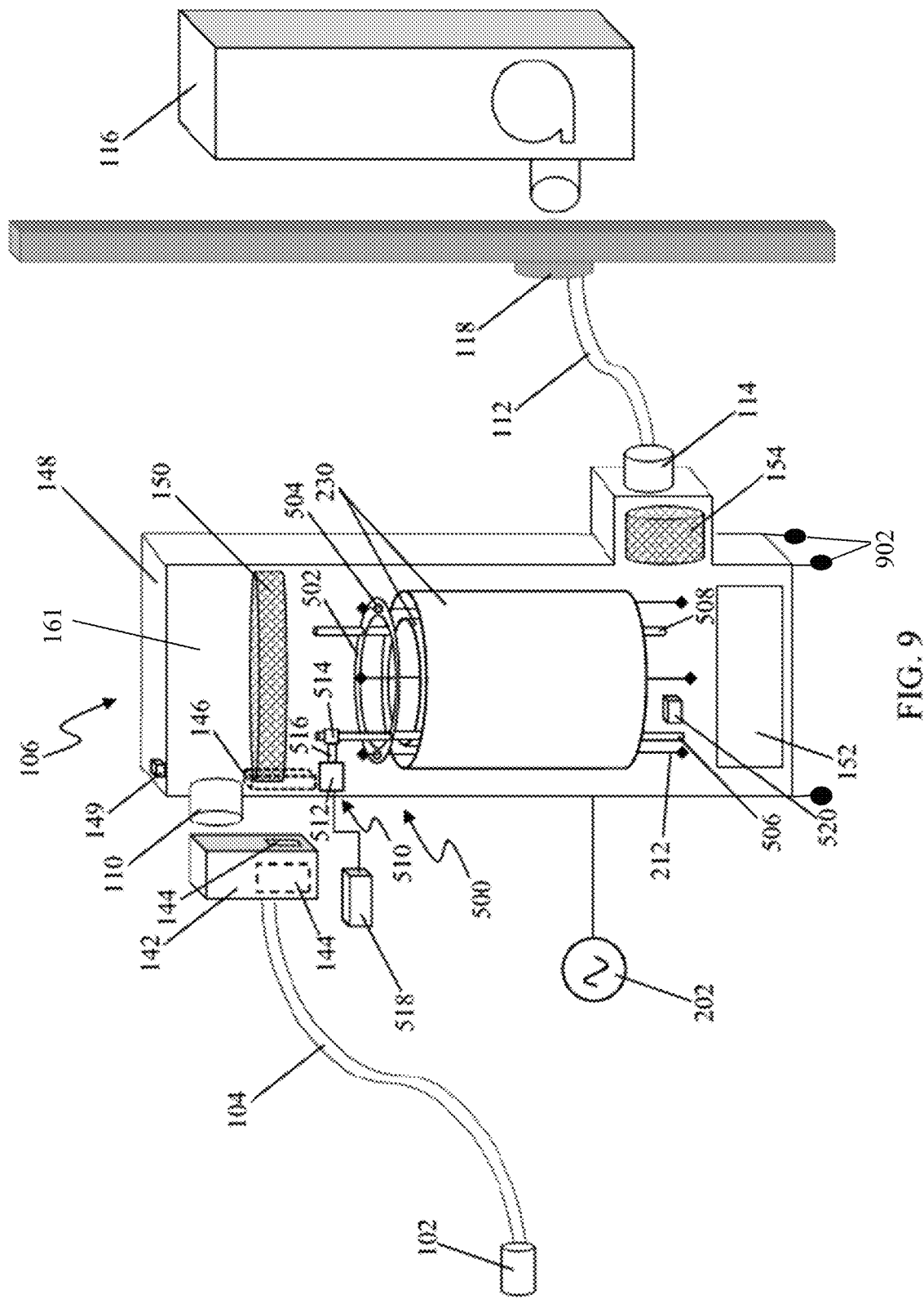
FIG. 9 illustrates another schematic of an exemplary electrostatic precipitator according to an embodiment present disclosure.

As illustrated in FIG. 9, in another embodiment, the electrostatic collection cell 200 may comprise a plurality of coaxial hollow-cylindrical collection tubes 230. The collection tubes 230 may comprise an outer collection tube with additional collection tubes disposed coaxially and radially within. The longitudinal axes of the collection tubes 230 may be generally vertically oriented. At least one of the discharge electrodes 212 may be disposed generally coaxially through the radially innermost collection tube 230, additional discharge electrodes 212 may be disposed radially between the other collection tubes 230. The discharge electrodes 212 are in electrical communication with the electrical power source 202 for electrically charging particulate within the surgical smoke.

The collection surface of the collection tubes 230 and the discharge electrodes 212 are oppositely charged. In an embodiment, the power source 202 may be utilized to induce a negative voltage in the discharge electrodes 212 and to induce a positive voltage in the collection surface of the collection tubes 230. In another embodiment, the power source 202 may be utilized to induce a negative voltage in the discharge electrodes 212, and the collection surface of the collection tubes 230 may be connected to ground. In still another embodiment, the power source 202 may be utilized to induce a positive voltage in the discharge electrodes 212, and the collection surface of the collection tubes 230 may be connected to ground or have a negative voltage induced therein via the power source 202. In one embodiment, the electric potential difference between the discharge electrodes 212 and the collection surface of the collection tubes 230 is seven kilovolts ("7 kV"). The electric potential difference between the discharge electrodes 212 and the collection surface of the collection tubes 230 may be greater than 7 kV; however, undesirable electric arcing between the discharge electrodes 212 and the collection surface may occur at a high enough electric potential difference.

In an embodiment, the collection tubes 230 may be temporarily removed from the electrostatic precipitator assembly housing 148 to be cleaned prior to reinstallation. Alternatively, or in conjunction with being cleanable, the collection tubes 230 may be disposable and replaceable. In embodiments where the collection surface of the collection tubes 230 is not connected to ground during operation, the opening of an access panel 213 in the housing 148 connects the collection surface to ground. Connecting the collection surface to ground prior to removal ensures the prevention of harm to any person removing the collection tubes 230 from the electrostatic precipitator assembly 106 due to residual voltage in the collection surface.

With continued reference to FIG. 9, in another embodiment, the electrostatic precipitator assembly 106 may include a cleaning element 500 to at least partially remove the precipitate and accumulated particulate from the collection surface of the collection cell 200. The cleaning element 500 may comprise an annular blade 502 located such that the blade 502 may move between a radially outer collection surface and a radially inner collection surface of the collection tubes 230. The radially outer and radially inner edge of the blade 502 is disposed such that it will contact the collection surfaces as the blade descends through the collection tubes 230. In an embodiment, the blade 502 may comprise an elastomeric material. One or more apertures 504 may be disposed through the blade 502 to accommodate discharge electrodes 212 disposed therethrough. Additionally, the blade 502 may be fixedly coupled with a first shaft 506 capable of linear actuation within the housing 148. A second shaft 508 may be slidably coupled with the blade 502 to support the orientation of the blade 502 during actuation thereof. An actuator assembly 510 may be located within the housing 148 to actuate the blade 502 through the collection tubes 230. In an embodiment, the actuator assembly 510 may comprise a power source 512 such as a brushless direct current (BLDC) motor. The power source 512 may be coupled with a pinion gear 514 via a shaft 516. The pinion gear 514 may be in meshed engagement with a plurality of teeth on the shaft 506. In other embodiments, the actuator assembly 510 may comprise other linear actuators.

Figure 7:
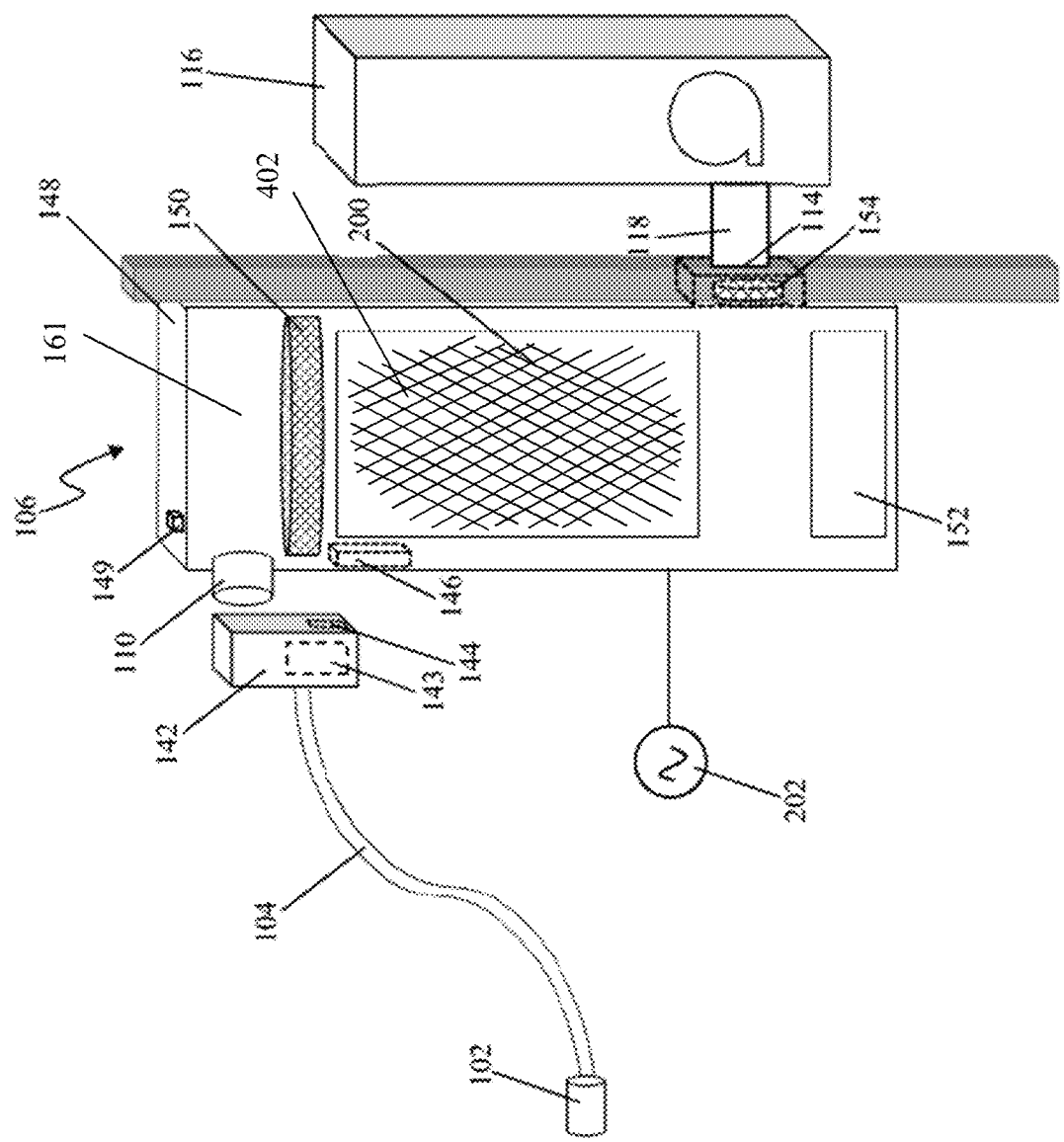
FIG. 7 illustrates a schematic of an exemplary evacuation system according to another embodiment of the present disclosure.

In another embodiment, the electrostatic collection cell 200 may include a collection surface comprising a mesh 402 (shown in FIG. 7). The mesh 402 may comprise a screen, an open-cell metal foam, wire wool, or wire sponge. As described in the embodiments above, the potential difference between the discharge electrodes 212 and the collection surface facilitates accumulation of ionized particulate on the collection surface. The mesh 402 collection surface attracts ionized particulate from the surgical smoke while having minimal impact on the flow rate through the fluid evacuation system 100.

Figure 8:
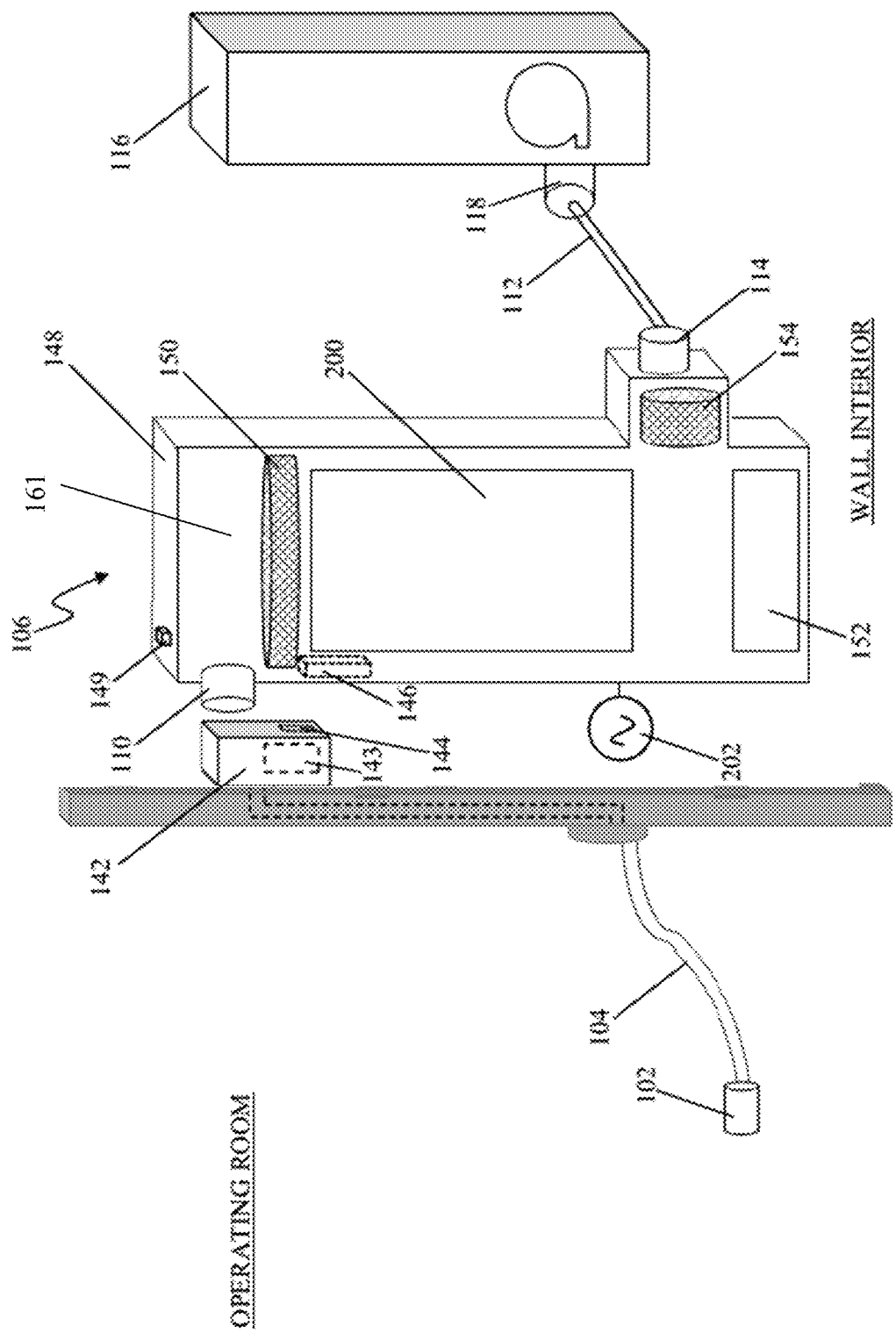
FIG. 8 illustrates a schematic of an exemplary evacuation system according to yet another embodiment of the present disclosure.

With reference now to FIG. 1, the electrostatic precipitator assembly 106 may be located adjacent to the vacuum power source inlet 118. In this embodiment, the electrostatic precipitator assembly 106 may be moved around an operating area for the convenience of medical staff or users. The electrostatic precipitator assembly 106 may comprise selectively locking wheels 902 to increase the mobility of the electrostatic precipitator assembly 106. In another embodiment, as illustrated in FIG. 7, the electrostatic precipitator assembly 106 may be mounted on a wall 160 at or adjacent to the vacuum power source inlet 118. In this embodiment, a second tube 112 for fluid communication between the electrostatic precipitator assembly fluid outlet 114 and the vacuum power source 116 may be obviated. In yet another embodiment, as illustrated in FIG. 8, at least a portion of the electrostatic precipitator assembly 106 may be located within the wall 160.

In an embodiment, the controller 318 may include a processor operating under the control of a set of programming instructions, which may also be referred to as software. The controller 318 may also include a memory 319 in which programming instructions are stored and a processor 321 (shown in FIG. 4). The memory 319 can also store identification codes and collection surface electrical charge records over a period of time. The controller 318 may output signals to the actuator assembly 310 to operate the cleaning element. The controller 318 may also output signals to a user interface 323 operable to interact with a user to indicate when the collection surface should be cleaned or replaced. The user interface 323 may be included as a part of the electrostatic precipitator assembly 106 or may be included in a freestanding device. Embodiments provide that a user is able to activate the electrostatic precipitator 106, surgical apparatus 102, and/or vacuum source 116 through user interface 323. Embodiments of user interface 323 include keypads, touch screens, buttons, computer interfaces and the like.

In practice, embodiments of the present disclosure provide a vacuum power source 116 operable to create or urge a flow of fluid from surgical apparatus 102 through tube 104, fluid inlet 110, hollow conduit 161, filter 150, collection cell 200, collection tray 152, fluid outlet 114, to vacuum power source 116. Fluid and particulates that enter hollow conduit 161 flow to filter 150 such that larger particulates and smoke are filtered out of the flow of fluid by filter 150. The flow of fluid is then electrically charged by electrodes (e.g., 212, 222, etc.) such that they are either negatively or positively charged. The electrically charged flow of fluid then passes through or over collection cells (e.g., 200) wherein collection cells are oppositely charged from that of the electrodes. The passing flow of fluid is attracted towards and accumulates on the collection cells. Any remaining flow of fluid then passes over or adjacent to the collection tray 152 and out of electrostatic precipitator 106 to vacuum power source 116. In some embodiments, collection cells 200 can be cleaned by cleaning elements 300 when the collection cells accumulate enough charged particulates such that they cannot attract anymore particulates. In other embodiments, collection cells 200 are removably affixed within electrostatic precipitator such that they accumulated particulates can be manually removed.

Figure 10:
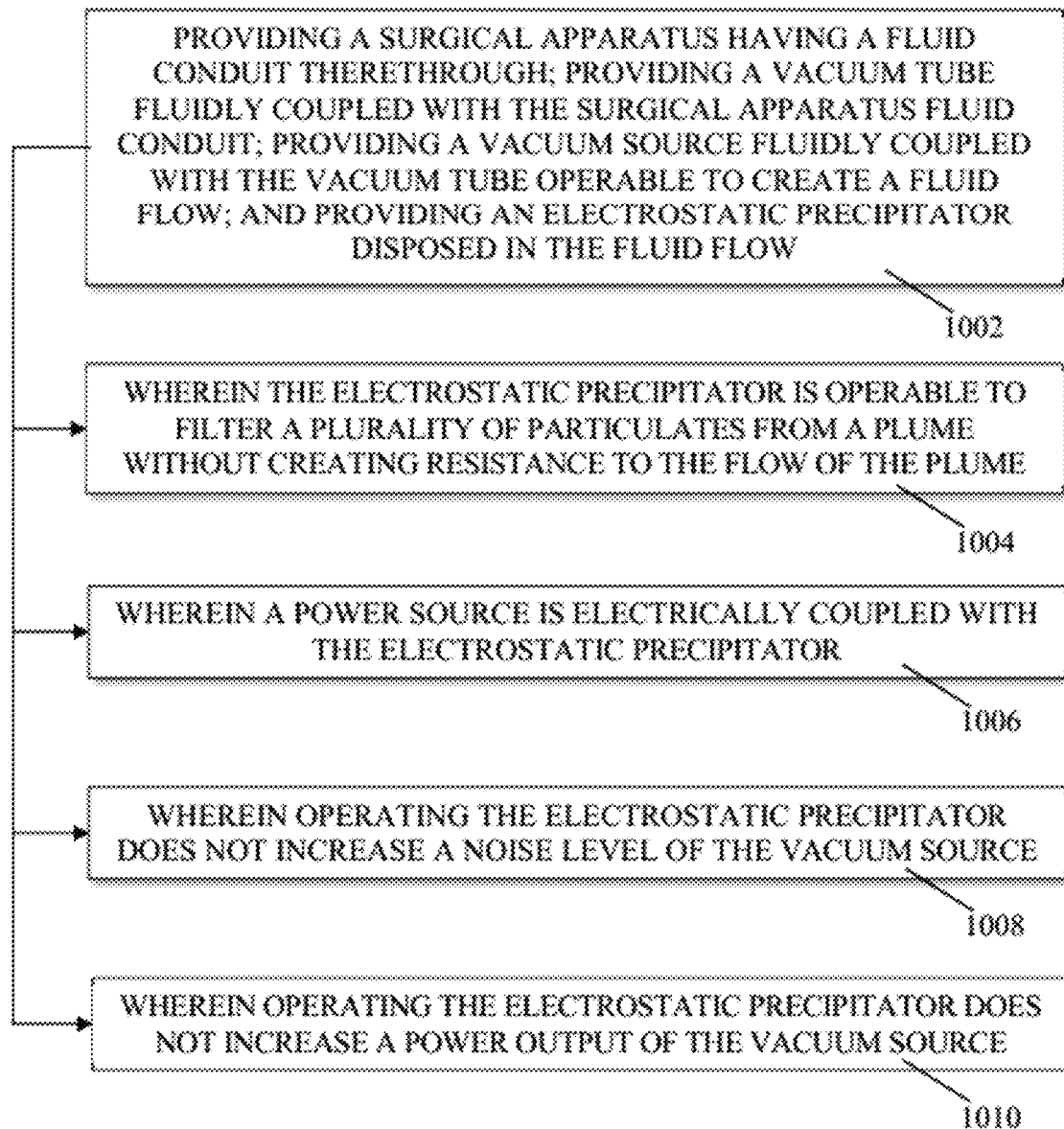
FIG. 10 illustrates a flow diagram in accordance with a method and apparatus for performing exemplary embodiments of the present disclosure.

Reference is now made to FIG. 10, depicting a simplified logic flow diagram in accordance with an embodiment of a method of providing a fluid evacuation system. The method begins at block 1002 which states providing a surgical apparatus having a fluid conduit therethrough; providing a vacuum tube fluidly coupled with the surgical apparatus fluid conduit; providing a vacuum source fluidly coupled with the vacuum tube operable to create a fluid flow; and providing an electrostatic precipitator disposed in the fluid flow. Block 1004 then indicates wherein the electrostatic precipitator is operable to filter a plurality of particulates from a plume without creating resistance to the flow of the plume. Block 1006 states wherein a power source is electrically coupled with the electrostatic precipitator. Block 1008 relates wherein operating the electrostatic precipitator does not increase a noise level of the vacuum source, and block 1010 indicates wherein operating the electrostatic precipitator does not increase a power output of the vacuum source.

The logic diagram of FIG. 10 may be considered to illustrate the operation of a method, or a result of execution of computer program instructions stored in a computer-readable medium. The logic diagram may also be considered a specific manner in which components of a device are configured to cause that device to operate.

It should be appreciated that while embodiments of electrostatic precipitator assembly 106 described above have been described as having two particulate filters and an electrostatic collector, embodiments include electrostatic precipitator assembly 106 having one or zero particulate filters.

One or more features of the embodiments described herein may be combined to create additional embodiments which are not depicted. While various embodiments have been described in detail above, it should be understood that they have been presented by way of example, and not limitation. It will be apparent to persons skilled in the relevant arts that the disclosed subject matter may be embodied in other specific forms, variations, and modifications without departing from the scope, spirit, or essential characteristics thereof. The embodiments described above are therefore to be considered in all respects as illustrative, and not restrictive. The scope of the invention is indicated by the appended claims, and all changes that come within the meaning and range of equivalents thereof are intended to be embraced therein.

The invention claimed is:

1. A fluid evacuation apparatus, comprising:
   a surgical apparatus having a fluid conduit therethrough;
   a vacuum tube fluidly coupled with the fluid conduit;
   an electrostatic precipitator fluidly coupled with the fluid conduit, the electrostatic precipitator comprising a housing and at least one collection surface operable to attract ionized particulate; and
   a vacuum source fluidly coupled with the vacuum tube, wherein the vacuum source is operable to create a flow of fluid through the fluid conduit, the vacuum tube and the electrostatic precipitator, wherein the electrostatic precipitator comprises a collection cell that is electrically charged to at least partially capture oppositely charged particulates in the flow of fluid, wherein the vacuum tube comprises a first section fluidly coupled between the surgical apparatus and the housing, and a second section fluidly coupled between the housing and the vacuum source.

2. The fluid evacuation system according to claim 1, wherein the electrostatic precipitator is located along the vacuum tube.

3. The fluid evacuation system according to claim 1, the fluid evacuation system further comprising a High Efficiency Particulate Air filter located in the flow of fluid downstream of the electrostatic precipitator.

4. The fluid evacuation system according to claim 1, the fluid evacuation system further comprising a power source electrically coupled with the electrostatic precipitator, the power source operable to electrically charge the collection surface.

5. The fluid evacuation system according to claim 1, the fluid evacuation system further comprising a power source electrically coupled with the electrostatic precipitator, and wherein the surgical apparatus comprises at least a first button and a second button, the at least one of the first and second buttons is operable to control the power source.

6. The fluid evacuation system according to claim 1, the fluid evacuation system further comprising a valve operable to interrupt the flow of fluid through the fluid evacuation system during operation of the vacuum source.

7. The fluid evacuation system according to claim 6, wherein the valve is located in a housing of the electrostatic precipitator, and wherein the valve is located within an inlet port of the housing, and wherein a valve button is operable to open and close the valve.

8. A method comprising:
   providing a surgical apparatus having a fluid conduit therethrough;
   providing a vacuum tube fluidly coupled with the fluid conduit;
   providing a vacuum source fluidly coupled with the vacuum tube, wherein the vacuum source is operable to create a flow of fluid; and
   providing an electrostatic precipitator disposed in the flow of fluid, wherein the electrostatic precipitator comprises a housing and is operable to filter a plurality of particulates from a plume without creating resistance to the flow of the plume, wherein the vacuum tube comprises a first section fluidly coupled between the surgical apparatus and the housing, and a second section fluidly coupled between the housing and the vacuum source.

9. The method according to claim 8, the method further comprising providing a power source electrically coupled with the electrostatic precipitator.

10. An electrostatic precipitator, comprising:
a housing comprising an inlet port and an outlet port in fluid communication;
a vacuum tube fluidly coupled with the inlet port and the outlet port;
an electrode located within the housing and electrically coupled with a power source, the electrode operable to ionize a plurality of particulates in a plume;
a collection surface located downstream of the electrode operable to attract the plurality of particulates;
a collection tray located under the collection surface; and
a cleaning element located within the housing operable to at least partially remove precipitate from the collection surface to the collection tray, wherein the vacuum tube comprises a first section fluidly coupled between a surgical apparatus and the housing, and a second section fluidly coupled between the housing and a vacuum source.

11. The electrostatic precipitator according to claim 10, wherein the collection surface comprises a radially interior surface of a tube, and wherein a longitudinal axis of the collection surface is vertically disposed.

12. The electrostatic precipitator according to claim 11, wherein the electrode comprises a wire located coaxially within the tube.

13. The electrostatic precipitator according to claim 11, wherein the cleaning element comprises a planar elastomeric blade, an aperture located through the blade, wherein the electrode is located coaxially through the aperture, a shaft coupled with the blade, and an actuator coupled with the shaft operable to move the blade at least partially through the tube.

14. The electrostatic precipitator according to claim 13, the electrostatic precipitator further comprising a controller electrically coupled with the actuator, and a sensor located adjacent to the collection surface and electrically connected with the controller, wherein the controller is operable to activate the actuator when the electric charge of the collection surface is below a predetermined value.

15. The electrostatic precipitator according to claim 10, wherein the collection surface comprises at least one of (i) at least two coaxially nested tubes, (ii) at least three hexagonal tubes disposed in a honeycomb configuration, and (iii) a vertically disposed plate.

16. The electrostatic precipitator according to claim 10, wherein the electrostatic precipitator is fluidly coupled at the inlet port to a manifold located adjacent to an exterior of the inlet port, the manifold further comprising a radio-frequency identification tag in communication with a radio-frequency identification reader located in the housing, and wherein the manifold comprises a fluid trap.

17. The electrostatic precipitator according to claim 10, the electrostatic precipitator further comprising a filter located in the housing adjacent to the inlet port, wherein the filter is operable to remove coarse particulate from a flow of fluid from the inlet port, the electrostatic precipitator further comprising a second filter located in the housing adjacent to the outlet port, wherein the second filter is operable to remove particulate from a flow of fluid to the outlet port.

* * * * *